(12) United States Patent
Barathur et al.

(10) Patent No.: US 8,524,774 B1
(45) Date of Patent: *Sep. 3, 2013

(54) TOPICAL TWO STEP POLYTHERAPY FOR TREATMENT OF PSORIASIS AND OTHER SKIN DISORDERS

(75) Inventors: Raj R. Barathur, Escondido, CA (US); Jack Bain Bookout, San Diego, CA (US)

(73) Assignee: Cymbiotics, Inc., Escondido, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/596,072

(22) Filed: Aug. 28, 2012

(51) Int. Cl.
*A61K 31/23* (2006.01)
*A61K 9/00* (2006.01)
*A61K 9/70* (2006.01)

(52) U.S. Cl.
USPC ............................ 514/552; 424/400; 424/449

(58) Field of Classification Search
USPC ........................................................ 514/552
See application file for complete search history.

(56) References Cited

U.S. PATENT DOCUMENTS

2011/0065627 A1 * 3/2011 Barathur et al. ............... 514/1.1

* cited by examiner

*Primary Examiner* — Blessing Fubara
*Assistant Examiner* — Jennifer Berrios

(57) ABSTRACT

A process for treating psoriasis and similar skin disorders whereby two formulations are used. The first formulation in a cream, gel, lotion, foam or ointment base is used two or more times daily, and contains effective amounts of (but not limited to) methylcobalamin, niacinamide, select cetylated fatty esters, and antioxidants. This formulation is used to suppress immunoproliferative and inflammatory mediated activities that play significant roles in hyperproliferation and erythema. The second formulation, used selectively to reduce plaque thickening and to reduce irritation, contains effective amounts of (but not limited to) salicylic acid and select cetylated fatty esters in a cream, gel, lotion or ointment base, with pH optimized for exfoliation properties. The unique combination of salicylic acid (or other β- or α-hydroxy acid) and cetylated fatty esters provides keratolytic activity while suppressing irritation and inflammation. The invention for this novel two-step polytherapy, are disclosed including the mode of sequential administration.

8 Claims, 1 Drawing Sheet

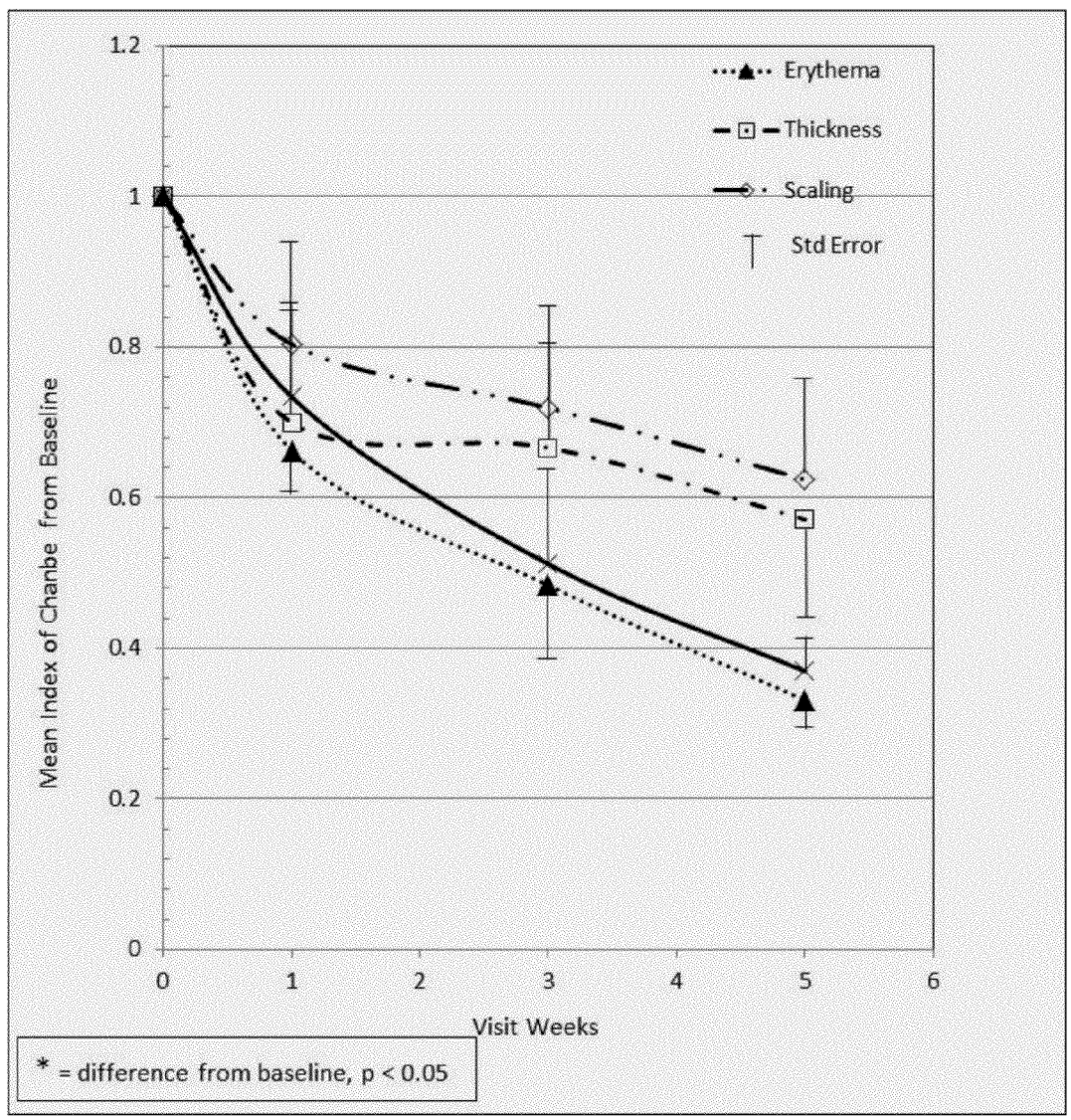

TOPICAL TWO STEP POLYTHERAPY FOR TREATMENT OF PSORIASIS AND OTHER SKIN DISORDERS

CROSS-REFERENCE TO RELATED APPLICATIONS

Not applicable.

STATEMENT REGARDING FEDERALLY SPONSORED RESEARCH OR DEVELOPMENT

Not applicable

TECHNICAL FIELD

The present invention relates to the use of two separate topical formulations in a combo formulation containing combinations of complimentary medicinal agents that, when used in topical applications sequentially, augment and enhance the treatment of psoriasis and similar disorders or manifestations of the skin.

BACKGROUND OF INVENTION

1. Field of the Invention

The background of this invention describes psoriasis and related skin disorders with emphasis on treatments using topical application formulations. This background is given without limiting the scope of the invention as to its application or utilization. The use of this invention with or without phototherapy for example, is envisioned as a potential application.

Psoriasis is a lifelong inflammatory disease of the skin, ensuing from a multiplicity of genetic and environmental factors and characterized by hyperproliferation of abnormally differentiating keratinocytes and underlying erythema from inflammatory mediated activities. Remissions and exacerbations are often spontaneous. When exacerbations of parakeratotic scales are present, they are often adjacent to symptomless skin. It is currently proposed that the hyperproliferation of keratinocytes, altered differentiation and angiogenic tissue responses result from the release of cytokines, chemokines and growth factors from dendritic antigen presenting cells and T cells, which have been stimulated by extrinsic or intrinsic factors or both. The review of immunopathogenesis and genetics of psoriasis [Nickoloff B J & Nestle F O, J Clin Invest, 113, pp. 1664-1675 (2004)] is hereby incorporated by reference.

Ideally, therapeutic approaches should address the process causing conversion of symptomless skin to psoriatic plaques and remove or reduce the processes by which the plaque is sustained. Much current therapeutic research is devoted to addressing underlying immune factors: T cell trafficking, T cell activation, cytokine inhibitors and counteroffensive strategies. While addressing immune dysfunctions, therapeutic approaches should maintain the normal physiologic processes in the skin that constitute immunological vigilance and barrier defense.

Conventional treatments do not provide efficacy and safety that would be considered ideal. For example, corticosteroids, the most common prescribed treatment, provide generalized, but not selective immuno-suppression, and, while acceptable therapeutic results can be obtained, much of utility is limited due to potential tachyphylaxis, rebound effects and skin thinning associated with prolonged use [Lebwohl et al., Int J Dermatol, 34, pp. 673-84 (1995)]. Other examples would be treatments with various vitamin D3 derivatives, which have been found to be as potent as midrange topical steroids; however, percutaneous absorption can be associated with disruption of normal calcium metabolism [Dubertret L, et al., J Am Acad Derm, 27(6), pp. 983-88 (1992); Kragballe M & Iversen L, Dermatol Ther, 11, pp. 137-41 (1993); Fullerton A, et al., Acta Derm Venerol (Stockh), 76, pp. 194-202 (1996)]. Therefore, careful dose administration is necessary to avoid changes in serum calcium levels and calcium-bone metabolism. Other therapies involving the use of Vitamin A and C systemic therapy have shown only questionable value. The retinoid tazarotene, for example, lacks the skin thinning effects associated with corticosteroids; however, response to this vitamin A derivative is delayed compared to steroids and may irritate the skin [Sander P, et al., Hautarzt, 50, pp. 723-27 (1999)]. Because of risk of birth defects, women of childbearing age must take measure to prevent pregnancy when using tazarotene. Anthralin applications can reduce hyperproliferation and inflammation [Lowe N J, et al., J Am Acad Derm, 10(1), pp. 69-72 (1984)]; however, it stains skin and all material contacted. In addition, anthralin carries a risk of skin irritation, making it unsuitable for acute or actively inflamed eruptions. In fact, many treatment combinations could be presented here that would show only limited efficacy and a variety of undesirable side effects. With some applications, such as that of coal tar applications to affected areas, conditions were often found to worsen. The following are listed as examples of other various approaches that have been developed for treating psoriasis: U.S. Pat. No. 4,788,057 to Catapano, issued Nov. 29, 1988 (typhoid vaccine); U.S. Pat. No. 4,853,388 to Ohtsu and Yabushita, issued Aug. 1, 1989 (cytotoxic agents); U.S. Pat. No. 5,501,705 to Fakhri, issued May 26, 1996 (electric currents); U.S. Pat. No. 5,527,350 to Grove et al., issued Jun. 18, 1996 (pulsed infrared laser); U.S. Pat. No. 5,833,996 to Stanford et al., issued Nov. 10, 1998 (*Mycobacterium vaccae* extract); U.S. Pat. No. 5,836,999 to Eckhouse and Kreindel, issued Nov. 17, 1998 (pulsed electromagnetic radiation); U.S. Pat. No. 5,976,505 to Henderson, issued Nov. 2, 1999 (liquid nitrogen or liquid nitrous oxide).

Most patients having mild-to-moderate psoriasis initially receive topical therapy. But treatment choices require consideration of the type of psoriasis, location of lesions and degree or extent of involvement. It is necessary for the treatment regimen to be flexible since treatment response is not always predictable. The present invention relates to significant improvements in the treatment for psoriasis and similar manifestations of the skin. The invention provides necessary treatment flexibility while improving treatment performance and reducing undesirable adverse effects.

2. Treatment Applications for Psoriasis that are Related to this Invention and Proposal A review of the state of the art, in respect to the many treatment combinations for psoriasis, reveals prior art germane to the formulations utilized in this invention. Although the formulations, as described in this invention have not been previously disclosed, the prior art formed an important contribution to the discovery that certain active ingredients when combined together provided beneficial responses. We present the following as background in support of the proposed formulations.

3. Cobalamins

Organometallic vitamin $B_{12}$ derivatives (cobalamins) have been used for psoriasis treatment with promising results [Cohen E L, Practitioner, 181, pp. 618-620 (1958); Ruedeman R and Albany N.Y., Arch Derma Syph (Chic.), 69, pp. 738 (1954)]. Studies by Cakmak S K, et al. [J Eu Acad Derm Vener, 23, pp. 300-303 (2009)] indicate an inverse relationship between the levels of vitamin B12 and psoriasis severity. Inherited errors in cobalamin metabolism are characteristic of psoriasis patients [Ueland P M, et al., in Vascular Diagnostics, pp. 75-84]. In vitro studies also demonstrated immunomodulatory effects of cobalamins on T lymphocytes and cytokines [Sakane T et al., J Clin Immunol, 2, pp. 101-109 (1982); Yamashiki M et al. J Clin Lab Immunol, 37, pp. 173-182 (1992)]. Immunomodulatory effects include the increased induction of T-suppressor cells [Sakane T et al., J Clin Immunol, 2, pp. 101-109 (1982)], and Yamashiki et al. [J Clin Lab Immunol, 37, pp. 173-182 (1992)] showed a dose dependent in vitro suppression of IL 6 and INF-γ in the presence of vitamin $B_{12}$. Cobalamins, like Methylcobalamin (MeCbl), also are effective scavengers of nitric oxide [Stucker M, et al., Br J Derm, 150, pp. 977-983 (2004)], and topical applications result in significant decreases in pruritus and erythema. Inflammation in psoriasis may be linked with increased levels of nitric oxide. The itching and dermatitis conditions like those found in psoriasis and atopic dermatitis are a direct result of inflammatory cytokines. Recent research, therefore, show that vitamin $B_{12}$ plays a useful role in inhibiting production of inflammatory cytokines and trapping nitric oxide, thus making the latter less harmful. A large portion of topically administered methylcobalamin is absorbed via the skin and remains bio available to act on the T cells for a longer period of time. No drug resistance has been reported and no skin irritation occurs compared to Calcipotriol skin treatments. U.S. Pat. No. 5,798,341, Klingelholler, issued Aug. 25, 1998 presented a topical treatment method for treating hyperproliferative skin disorders, including psoriasis, using cobalamins. No teaching from this patent predicts the invention which we are proposing, and the formulations proposed for protection under their patent do not show a direct or implied relationship to our invention.

4. Niacinamide

Niacinamide (or nicotinamide) derivatives have been disclosed previously as effective medicaments for the treatment of psoriasis (for example, U.S. Pat. No. 4,067,975, Yu R J and Van Scott E J, issued Jan. 10, 1978; U.S. Pat. No. 4,258,052, Yu R J et al., issued Mar. 24, 1981; U.S. Pat. No. 6,248,763 B1 to Scivoletto, issued Jun. 19, 2001). In Patent Application US 2009/0131488 A1 to Harel A, et al. published May 21, 2009 a composition containing nicotinamide and calcipotriol and methods for use in treatment of hyperproliferative dermal diseases are described. Niacinamide is an inhibitor of poly (ADP-ribose) polymerase-1 (PARP-1) that, through enhancement of nuclear kappa B-mediated transcription, plays a pivotal regulatory role in the expression of inflammatory cytokines, chemokines, adhesion molecules, and inflammatory mediators [Namazi M R, FASEB J, 17, pp. 1377-1379 (2003)]. It is also a potent phosphodiesterase inhibitor, suppressing neutrophil chemotaxis and mast cell histamine release. EP 1,651,641 B1 to Barber C G, issued May 23, 2007 describes the utility of specific nicotinamide derivatives as phosphodiesterase (PDE4) inhibitors for treatment of various inflammatory diseases. Nicotinamide is also known to be a powerful moisturizing agent.

5. Curcumin

The role of curcumin in treatment of psoriasis and other inflammatory skin diseases is reviewed by Aggarwal B B and Harikumar K B [Int J Biochem Cell Biol, 41, pp. 40-59 (2009)] and is incorporated herein for reference. U.S. Pat. No. 6,673,843 B2, Arbiser J L, issued Jan. 6, 2004 discloses using 0.5% to 5% of curcumin and curcumin analogs (demethoxycurcumin, bisdemethoxycurcumin) as angiogenesis inhibitors to treat skin disorders; a possible use with psoriasis is postulated but not mentioned in claims. Curcumin plays a key treatment role as an antioxidant but is also known to exhibit antimutagenic activities (Ames *Salmonella* test) and to produce biochemical effects similar to those of chemopreventive polyphenols [Stoner G D, J. Cell. Biochem., 59 (s22), pp. 169-80 (1995)]. Curcumin has been demonstrated to inhibit several signal transduction pathways, including those involving protein kinase C, the transcription factor NF-kB, arachidonic acid metabolism, phospholipase A2 bioactivity, and epidermal growth factor (EGF) receptor autophosphorylation [Lu et al., Carcinogeneisis 15: 2363-70 (1994); Huang et al, Proc Natl Acad Sci USA 88: 5292-96 (1991); Korutla et al., Carcinogenesis 16: 1741-1745 (1995); Rao et al. Carcinogenesis 14: 2219-2225 (1993).] U.S. Pat. No. 5,401,504 to Das et al., issued March, 1995 describes the oral or topical administration of turmeric to humans to promote wound healing. New applications for various protein kinase C inhibitors, including curcumin and tetrahydrocurcumin, for wound and scar healing was amplified in U.S. Pat. No. 6,306,383 B1 to Crandall W T, issued Oct. 23, 2001.

6. Keratolytic Agents

The use of keratolytic agents (β- or α-hydroxy acids) is well established in the treatment of many dermatologic conditions, including psoriasis. Salicylic acid is a frequently used keratolytic agent with several actions that are important to the treatment of psoriasis. It reduces intercellular cohesiveness within the layers of the stratum corneum and at the lower pH, increases hydration and softening [Huber C and Christophers F. Arch Derm Res, 257, pp 293-297 (1977); Davies M and Marks R, Br J Dermatol, 95, pp. 187-192 (1976)].

The combination of salicylic acid with other agents, such as corticosteroids, is not unique. Carroll C L, et al. [Arch Dermatol, 141, pp. 43-46 (2005)] describes a combined topical application of 0.1% tacrolimus ointment with 6% salicylic acid gel for treatment of psoriasis plaque. Both applications were applied together twice daily. The combined treatment showed greater improvement than treatment with salicylic acid alone. Adverse events are usually minor, and include burning at the application site. The other adverse effect attributed to salicylic acid was peeling. These secondary effects can reduce tolerance and in turn compliance by the patients. U.S. Pat. No. 6,440,465 B1, Meisner, issued Aug. 27, 2002 describes topical compositions using glucosamine as an emollient and incorporating antioxidants such as oleuropein and berberine and keratolytic substances such as coal tar extract or salicylic acid. This topical formulation was applied to treating psoriasis, atopic dermatitis and related skin ailments. Related compositions broaden applications of the previous patent in U.S. Pat. No. 7,670,620 B2, Meisner, issued Mar. 2, 2010 to treat inflammatory skin ailments: psoriasis, dermatitis, eczema, atopic dermatitis. Patent Application US 2005/0003023 A1 to Meisner published Jan. 6, 2005 also further extends the previous issuances. U.S. Pat. No. 4,740,372 to Boncic, issued Apr. 26, 1988 describes a topical application for treating psoriasis in a specific formulation containing salicylic acid, tetracycline, gentamycin sulfate and neomycin sulfate. U.S. Pat. No. 3,879,537 describes the use of α-hydroxy acids, α-keto acids and related compounds for topical treatment of ichthyotic conditions; U.S. Pat. No.

3,920,835 also describes the use of certain α-hydroxy acids, α-keto acids and their derivatives for topical treatment of dandruff, acne, and palmar and plantar hyperkeratosis. The following are listed as examples of various other approaches to treat skin disorders (but not psoriasis) that have been developed: U.S. Pat. No. 5,741,497 to Guerrero et al. Issued Apr. 21, 1998 (skin wrinkling); U.S. Pat. No. 4,126,681 to Reller, issued Nov. 21, 1978 (skin ointment). In many studies, the addition of salicylic acid tended to improve treatment efficacy when mild secondary effects were properly addressed. The utility of compartmentalizing the keratolytic agent for sequential application to avoid adverse secondary effects is a novel teaching in this proposal.

7. Applications of Cetylated Fatty Esters in Immune Mediated Inflammation

The medicinal utilization of cetylated fatty acids were first described in U.S. Pat. No. 4,049,824, Diehl, issued Sep. 20, 1977 and U.S. Pat. No. 4,113,881, Diehl, issued Sep. 12, 1978. These patents provide examples for the oral utilization of cetyl myristoleate in effective amounts for the treatment of inflammatory rheumatoid arthritis in mammals. In U.S. Pat. No. 5,569,676, Diehl, issued Oct. 29, 1996 extended treatment claims for cetyl myristoleate to treat osteoarthritis and to include topical and parenteral modes of delivery. U.S. Pat. No. 6,417,227, Lord and Lytle, issued July, 2002 describes the use of cetyl myristoleate in the oral treatment of tendinitis, tenosynovitis, bursitis, chronic patellar tendinitis, Achilles tendinitis, fibrositis, inflammation of spine, colitis, bronchitis, polymyalagia rheumatic, Crohn's disease, primary biliary cirrhosis, pericarditis, ulcerative colitis and Sjogren's syndrome. Cetyl myristoleate, as described in this patent, when administrated in a dissolution resistant-coated capsule was noted to have therapeutic properties which could be applied to multiple condition types having associated inflammation and immune mediated pain. U.S. Pat. No. 6,677,321, Levin, issued Jan. 13, 2004 extended the oral administration of cetyl myristoleate for treating inflammatory diseases, when the cetyl myristoleate or one or more esters of unsaturated fatty acids and fatty alcohols are used in conjunction with at least one tetracycline compound, an NSAID, a COX-2 inhibitor, a corticosteroid, S-adenylmethionine or a synovial fluid supplement. For purposes of this disclosure, the cetylated fatty esters are defined as a select group of fatty acids that have been converted synthetically into cetyl esters, some with saturated and some unsaturated hydrocarbon chains, but with the number of carbon atoms of these chains ranging from 10 to 18 or more in length. The composition of these select groupings often includes but is not limited to the inclusion of cetyl myristoleate.

These patents are supported by numerous publications that define medicinal properties of the cetyl fatty esters. Research has shown that certain cetylated fatty esters act to relieve pain, improve joint mobility and return physical function due to affected joints in humans and in animal models. Other non-arthritic conditions that include myofascial pain syndrome and sports-related pain injuries have also demonstrated therapeutic potential. For reference in defense of these claims the following are added herein: Hesslink et al., J Rheumatol, 29, pp. 1708-1812 (2002); Kraemer et al., J Rheumatol, 31, pp. 767-774 (2004); Kraemer et al., J Strength Condit Res 19, pp. 475-480; Kraemer et al., J Strength Condit Res 19, pp. 115-121 (2005); Siemandi, Townsend Lett Doctors & Patients, August/September, pp 58-63 (1997); Sharan et al., Manual Therapy, 14 (supp), pp. S1-53 (2009); Edwards, J Nutr Environ Med, pp. 105-111 (2007); Hunter et al., Pharm Res, 47, pp. 43-47 (2003).

The utilization of cetylated fatty esters in the treatment of psoriasis and psoriatic arthritis has been proposed in U.S. Pat. No. 7,612,111 B2, Spencer and Millsap, issued Nov. 3, 2009 and U.S. Pat. No. 7,776,914 B2, Spencer and Millsap, issued Aug. 17, 2010. These patents suggest that psoriasis might be treated and/or prevented using an effective composition of lecithin fatty acid, and olive oil fatty acid, an esterified fatty acid and mixed tocopherols. However, these patents fall short in predicting the therapeutic applications as proposed in this application, nor are any claims for psoriasis treatment made in these patents. The invention as proposed in this application could not be deduced and certainly does not follow from the mention of psoriasis in these patents.

Further, the anti-inflammatory properties of these cetylated molecules have been demonstrated through successful transdermal applications for a number of inflammatory conditions. Even our own studies [Sharan D, et al., Manual Therapy, 14 (supp), pp. S1-53 (2009); Sharan D, et al., J Body Mov Therap, 15(3), pp. 363-374 (2011)] suggest that effective inflammatory treatment of myofascial pain syndrome with select cetylated fatty esters could be demonstrated through topical cream applications.

It is clear that the therapeutic utilization of cetylated fatty esters has a history of at least two decades. The efficacy of these medicinal actives is associated with the need of multiple dosing applications in order to get sufficient levels of absorption to obtain therapeutic results.

BRIEF SUMMARY OF INVENTION

The invention is comprised of two separate component applications that are administered to provide a complementary and more effective treatment while reducing the potential for undesirable adverse effects. The proper combinations, in which actives would be used, was not initially evident and required clinical trial and error. The selection of active agents to be used in the composition of the first component was derived largely from the complementary immunomodulating and curative properties of these agents. The composition is novel in design and transdermal application. However, it was not until the utilization of two separate treatment components (with optimization of the second component formulation) was tested that superior improvements with minimal secondary effects were achieved. It was also discovered that the two component administration provided improved versatility in addressing the various forms and severity of the psoriatic conditions and other skin disorders.

One object of this present invention is to address the underlying T-cell disorder that results in the inflammatory condition. The first component formulation (App A) was designed to be applied more universally to the skin, such that liberal applications can be applied to both symptomatic plaque areas, pre-symptomatic areas as well as to non-symptomatic skin, to suppress potential plaque development. It contains effective amounts of (but not limited to) methylcobalamin, niacinamide, cetylated fatty esters and antioxidants (tetrahydro curcumin and tocopherol acetate) in a cream, gel, lotion, foam or ointment base. This formulation is used to suppress inflammatory mediated activities that play significant roles in hyperproliferation and erythema. As indicated previously, these agents have been found effective in the treatment of psoriasis; however, the improved effectiveness of these agents when used as described in this invention has not been previously described and constitutes a new and novel approach. The composition of this formulation is designed to minimize any potential toxic effects. And the composition was selected to provide immunomodulation and protection from cell damage while reducing pain and pruritus sensations. Primary dosing criteria for the first component is based primarily on the degree or intensity of erythema and the area of plaque involvement.

Another object of this invention is to address plaque thickness or induration. The second formulation (App B) contains effective amounts of (but not limited to) select cetylated fatty esters and salicylic acid (or other β- or α-hydroxy acid) in a cream or ointment base, with pH optimized for exfoliation properties. Salicylic Acid is applied to plaque areas to remove the upper thickened stratum corneum without affecting the structure of the epidermis below. However, salicylic acid is an irritant; its use has sometimes resulted in a worsening of the condition it not administered properly. By providing this exfoliating agent with cetylated fatty esters in the second component, irritation is significantly reduced and controlled. The App B is formulated to be applied only to symptomatic plaque areas in a selective manner to reduce plaque thickening, and the applications are two or more times per week with frequency adjusted to severity in respect to thickness and degree of plaque scaling. In this way the primary metering criteria for App B is the degree of induration and the area of involvement. The proper administration in this manner provides a more effective treatment while minimizing irritation. The unique combination of cetylated fatty esters and salicylic acid provides keratolytic activity while suppressing irritation and inflammation. This combination is an innovative feature of this invention. While the hydroxyl acid acts as an exfoliating agent, the select combination of cetylated fatty esters, as described in this application, has been clinically proven to act on the inflammation pathways, reducing overall inflammation [Hesslink R et al., J Rheumatol, 29, pp. 1708-1712 (2002); Kramer W J et al., J Rheumatol, 31, pp. 767-774 (2003)]. In addition cetylated fatty esters are moisturizing and hydrating agents. To date, there have been no reported adverse events or resistance to cetylated fatty ester activity. The utility of compartmentalizing the cetylated fatty esters for sequential application to avoid adverse reduce inflammation and pruritis caused by Salicylic acid is a novel teaching in this proposal.

The two components of this invention have complimentary treatment effects. App B can be applied over areas, on which the first App A component has been previously applied. The treatment process is well tolerated with minimal concern for secondary adverse effects.

BRIEF DESCRIPTION OF THE DRAWING

FIG. 1 shows the mean indices of change from baseline for the total PASI score, erythema, thickness and scaling as a result of treatments with App A and App B over a 5 week period.

DETAILED DESCRIPTION OF THE PREFERRED EMBODIMENTS OF THE INVENTION

The novel approach to treatment of psoriasis and related skin manifestations is based on the formulation and administration of two separate component compositions. App A is formulated to be applied daily and at least twice each day, applied in circular motions to facilitate absorption, to symptomatic, pre-symptomatic and surrounding asymptomatic skin. Because this component is well tolerated, additional applications may be administered relative to the severity of the plaques and scaling that is present. App A can be applied to asymptomatic skin areas as a prophylactic measure to aid and prevent eruptions from occurring. App A acts to suppress immune activities that may stimulate hyperproliferation of the keratinocytes, reduce inflammation and pruritis, and also to provide moisturization and softening of the skin. The cetylated fatty esters in addition to being anti-inflammatory are humectants that hydrate and soften plaques, while the antioxidants employed in the formulation aid in reducing cell damage from free radicals. The cobalamin and niacinamide, in addition to suppressing immune activities that may stimulate hyperproliferation of the keratinocytes, also provide essential vitamins, which may have been depleted from the skin. In this manner, erythema is reduced while skin pH and barrier integrity dysfunctions are addressed.

However, App A is complemented through utilization of App B, as applied at less than the daily frequency of the first component. The second component, containing the keratolytic hydroxy acid, is applied 2-3 times each week, and as needed, to facilitate removal of the dead skin layers present in the plaques. Application frequency of App B can be adjusted based on severity (scaling and thickness) of involvement and on individual patient tolerance without reduction in benefits by limiting the first component application. The second component can be applied over the first component applications after absorption but it is not applied to asymptomatic skin areas, which could result in irritation of asymptomatic areas, and may lead to reduction in patient treatment compliance. The inclusion of the select cetylated fatty esters in the App B composition aids in reduction of potential irritation responses. In addition, the select cetylated fatty esters may play a role promoting collagen production.

1. The Disclosed Formulations for the First Component, App A

The composition of App A includes polar emulsifiers, humectants, emollients, anti-inflammatories, ionic salts, preservatives, thickening agents, antioxidants, fragrance and water in either a cream, gel, lotion, foam or ointment base. Suitable carriers, including water, polar solvents, oils and related ingredients, are chosen for their ability to dissolve or disperse the active ingredients as most suitable for therapeutic treatment use.

The incorporation of a cobalamin molecule is disclosed for this invention as a preferred component. One or more of the following cobalamins are for use in App A: methylcobalamin, hydroxocobalamin, adenosylcobalamin, cyanocobalamin, isovitamin B12, adenylpropylcobalamin, dihydroxypropylcobalamin, methyl-10-chlorocobalamin. The use of methylcobalamin is most preferred. The itching and dermatitis found in psoriasis and atopic dermatitis are a direct result of inflammatory cytokines. Recent research, therefore, show that vitamin $B_{12}$ plays a useful role in inhibiting production of inflammatory cytokines and trapping nitric oxide, thus making the latter less harmful. A large portion of topically administered methylcobalamin is absorbed via the skin and remains bio available to act on the T cells for a longer period of time. The concentration of cobalamin in App A preferred is 0.05-8%. Most preferred is 0.05 to 0.2% by weight of the total composition.

The incorporation of niacinamide or derivative compounds is disclosed for this invention as a preferred component. One or more of the following niacinamides can be used in App A: 6-aminonicotinamide, 6-carbamoylnicotinamide, 6-chloronicotinamide, 6-dimethylamino-nicotinamide, 6-aminonicotinic acid methyl ester, 6-hydroxy nicotinic acid, thionicotinamide, 2-aminopyrazinamide, 2-carbamoylpyrazinamide, 6-benzoylamino nicotinamide, 6-oxalylamino nicotinamide, 6-malonylamino nicotinamide, 6-succinylamino nicotinamide, 6-glutarylamino nicotinamide ethyo or methyl ester, 6-phosphorylamino nicotinamide, 1-methyl-6-keto-1,6-dihydronicotinamide, 1-methyl-6-keto-1,6-dihydronicotinic acid, methyl 1-methyl-6-keto-1,6-dihydronicotinate, ethyl 1-methyl-6-keto-1,6-dihydronicotinamide. Niacinamide is an inhibitor of poly (ADP-ribose) polymerase-1 (PARP-1) that, through enhancement of nuclear kappa B-mediated transcription, plays a pivotal regulatory role in the expression of inflammatory cytokines, chemokines, adhesion molecules, and inflammatory mediators which reduces inflammation in psoriasis. The concentration of Niacinamide in App A preferred is 1-10%. Most preferred is 2-5% by weight of the total composition.

A critical and preferred novelty of this invention is the inclusion of select cetylated fatty esters in both App A and App B component formulations. This addition to App A provides the anti-inflammatory properties that reduce the inflammatory manifestations of the skin disorder. The cetylated fatty esters are well tolerated, and there are no known toxicity issues in regards to increased concentrations from additional applications. The cetylated fatty esters for this disclosure have been defined as a select group of fatty acids that have been converted synthetically into cetyl esters, some fatty acids with saturated and some unsaturated hydrocarbon chains, but with the number of carbon atoms of these chains ranging from 10 to 18 or more in length. The composition of these select groupings often includes but is not limited to the inclusion of cetyl oleate, cetyl palmitoleate and cetyl myristoleate. Other fatty acids, which can be cetylated and utilized in the select groups, may be saturated, mono- to poly-unsaturated, or may contain functional groups such as methoxy-, amino- or ring structures. The concentration of individual cetylated fatty esters typically ranges from 1-60% of the select group, depending on the cetylated molecule. Also, depending on the condition being treated 3-12 cetylated fatty ester molecular forms may comprise the select group. The preferred formulations contain a concentration of 4-40% cetylated fatty esters. Most preferred concentrations for App A being 5-10%.

The inventors have previously described the use of cetylated fatty esters as penetrating agents for enhanced transdermal delivery of cobalamin molecules and derivative molecules. For reference, the complete contents of U.S. Patent Application 2011/065627 A1, filed on Oct. 29, 2009, are herein incorporated. U.S. patent application Ser. No. 13/049,557, Barathur and Bookout, submitted Mar. 16, 2011 also describes penetration properties of cetyl fatty esters and is herein incorporated as a further reference. The compositions of App A were designed to facilitate transdermal delivery of cobalamins, cobalamin derivatives, niacinamide and niacinamide deriviatives. Difference cetylated ester molecules are used based on the physic-chemical properties of these permeants.

Preferably, the polar solvent/emulsifier material with hydrophilic polar groups in this invention is propylene glycol. The polar solvent provides hygroscopic and miscible properties that allow solubility of critical compounds. A property of propylene glycol, critical for this disclosure, is its ability to hydrate the skin, bringing the flux of water molecules into the stratum corneum. Other polar solvents used instead of or in conjunction with propylene glycol include glycerol of glycerol esters, ethylene glycol, 1, 2, 6-hexane triol, 1,2,4-butane triol, Pleuronics (Poloxamers), propylene glycol ether of methyl glucose or sorbitol, PEG 40 hydrogenated castor oil, PeGlycated sorbitol, dimethicone copolyol, polyethylene glycol (preferably, PEG 50, PEG 100 and PEG 500) and water. One or more polar solvents may be used in combination in a final combined concentration of 5-30%.

Examples of surfactants suitable for the disclosed App A formulation that are pharmaceutically-acceptable would include one or more of the following: phosphatidylethanolamine, Tween 80, glycerol monooleate, sorbitan monooleate, sodium oleate, ascorbyl palmitate, stearyl citrate and benzalkonium chloride.

Examples of antioxidants suitable for the disclosed App A formulation include one or more of the following: a curcumin compound, tocopherols (such as tocopherol acetate or tocopherol succinate), ascorbic acid and its esters, alpha lipoic acid, thiourea, and chelating agents like EDTA and citric acid. A curcumin compound is defined as one of the following: curcumin, tetrahydrocurcumin, bisdemethoxycurcumin, demethoxycurcumin. Tetrahydrocurcumin and tocopherol acetate is most preferred for use in the App A formulation. One or more antioxidants may be used singly or in combination in a final concentration of 1-5%. The preferred antioxidants are tetrahydrocurcumin and tocopherol acetate.

Preferably, the pH of the formulations range from 5.0 to 7.0. The range of ph 6.0 to 7.0 is the most preferred range. Suitable agents acceptable for pH adjustments include one of the following: triethanolamine, diethanolamine, sodium hydroxide, potassium hydroxide or ammonia base.

The thickening agents composing the formulation base include but are not limited to carbomer polymers (Carbopol 940 NF, Carbopol 934 NF, Carbopol Aqua CC,), hydroxycellulose, polyvinylacetate, polybutylacrylate, PEG 100 stearate, polymethylacrylate, polydimethylsiloxane, hydrogels (e.g., high molecular weight polyvinylpyrrolidone, oligomeric polyethylene oxide, or a mixture thereof) and organogels. PEG 40 hydrogenated castor oil or polyethoxylated castor oil may be used for proper composition in conjunction with the thickening agents. Other suitable components such as cetostearyl alcohol, polysorbate 80, acetamide MEA, glycereth-26, lactamide MEA and glycerin may be included. One or more of the thickening agents may be used singly or in combination in a final concentration of 1-10%.

Example of preservatives include, but are not limited to benzalkonium chloride, cetrimide, benzoic acid, benzethonium chloride, imidizolidinyl urea, benzyl alcohol, isopropyl alcohol, triclosan, hydantoin derivatives, phenyoxyethol, imidazolidinylurea and parabens. Preferably the preservative used is benzoic acid, methyl paraben, or propyl paraben, or a mixture thereof.

2. The Disclosed Formulations for the Second Component, App B

The composition of App B includes keratolytic agents, polar emulsifiers, humectants, emollients, anti-inflammatories, ionic salts, preservatives, antioxidants, fragrance and water in either a cream, gel, lotion or ointment base. Suitable carriers, including water, polar solvents, oils and the like, are chosen for their ability to dissolve or disperse the active ingredients as most suitable for therapeutic treatment use.

The incorporation of a keratolytic compound is disclosed for this invention as a preferred component. The concentration preferred is 1-20%. Most preferred concentration for the keratolytic agent is 1 to 5% by weight of the total composition. One or more of the following keratolytic agents may be used in App B: Keratolytic agents—glycolic acid, salicylic acid, citric acid, isocitric acid, glucuronic acid, galacturonic acid, glucuronolactone, a-hydroxybutyric acid, lactic acid, mallic acid, mandelic acid, muric acid, pyruvic acid and esters thereof, β-phenyllactic acid, β-phenylpyruvic acid, β-hydroxybutyric acid, tartaric acid, tartronic acid. The use of salicylic acid is most preferred.

A critical novelty of this invention is the inclusion of select cetylated fatty esters in both component formulations. This addition to App B provides the anti-inflammatory properties that reduce inflammatory manifestations of the skin disorder. The cetylated fatty esters are well tolerated, and there are no known toxicity issues in regards to increased concentrations from additional applications. The cetylated fatty esters for this disclosure have been defined as a select group of fatty acids that have been converted synthetically into cetyl esters, some fatty acids with saturated and some unsaturated hydrocarbon chains, but with the number of carbon atoms of these chains ranging from 10 to 18 or more in length. The composition of these select groupings often includes but is not limited to the inclusion of cetyl oleate, cetyl palmitoleate and cetyl myristoleate. Other fatty acids, which can be cetylated and utilized in the select groups, may be saturated, mono- to poly-unsaturated, or may contain functional groups such as methoxy-, amino- or ring structures. The preferred formulations contain a concentration of 4-40% cetylated fatty esters. Most preferred concentrations for App B being 5-10%. The concentration of individual cetylated fatty acids typically ranges from 1-60% of the select group, depending on the cetylated molecule. Also, depending on the condition being treated 3-12 cetylated fatty ester molecular forms may comprise the select group. When cetylated fatty esters are included in App B, they reduce the inflammation, and irritation that may be caused by the keratolytic agent namely salicylic acid or others used to remove scales and reduce the thickening of lesions.

Preferably, the polar solvent/emulsifier material in this invention is propylene glycol. The polar solvent provides hygroscopic and miscible properties that allow solubility of critical compounds. A property of propylene glycol, critical for this disclosure, is its ability to hydrate the skin, bringing the flux of water molecules into the stratum corneum. Other polar solvents used instead of or in conjunction with propylene glycol include glycerol, ethylene glycol, 1, 2, 6-hexane triol, 1,2,4-butane triol, propylene glycol ether of methyl glucose or sorbitol, PEG 40 hydrogenated caster oil, dimethicone copolyol, and polyethylene glycol (preferably, PEG 50, PEG 100 and PEG 500). One or more polar solvents may be used in combination in final combined concentrations of 5-30%.

Examples of antioxidants suitable for the disclosed App B formulation include one or more of the following: tocopherols, ascorbic acid and its esters, alpha lipoic acid, thiourea, BHT and chelating agents like EDTA and citric acid. One or more antioxidants may be used singly or in combination in a final concentration of 1-5%. The antioxidants disodium EDTA and tocopherol acetate are most preferred for use in the App B formulation.

Preferably the pH of the App B formulations range from 4.0 to 6.0. The range of ph 4.5 to 5.5 is the most preferred range. Suitable agents acceptable for pH adjustments include one of the following: triethanolamine, diethanolamine, citric acid, sodium hydroxide, potassium hydroxide or ammonia base.

The thickening agents composing the formulation base of App B include but are not limited to carbomer polymers (Carbopol 940 NF, Carbopol 934 NF, Carbopol Aqua CC,), hydroxycellulose, polyvinylacetate, polybutylacrylate, PEG 100 stearate, polymethylacrylate, polydimethylsiloxane, hydrogels (e.g., high molecular weight polyvinylpyrrolidone, oligomeric polyethylene oxide, or a mixture thereof) and organogels. PEG 40 hydrogenated castor oil or polyethoxylated castor oil may be used for proper composition in conjunction with the thickening agents. Other suitable components such as acetamide MEA, glycereth-26, lactamide MEA and glycerin may be included. One or more of the thickening agents may be used singly or in combination in a final concentration of 1-10%. Also preferred compounds which serve as humectants and lubricants include one or more of the following at a concentration of 1-3%: amodimethicone, dimethicone, cyclomethicone, simethicone, stearoxy dimethicone and behenoxy dimethicone.

Example of preservatives include, but are not limited to benzalkonium chloride, cetrimide, benzoic acid, benzethonium chloride, imidizolidinyl urea, benzyl alcohol, isopropyl alcohol, triclosan, hydantoin derivatives, phenyoxyethol, imidazolidinylurea and parabens. Preferably the preservative is benzoic acid, methyl paraben, or propyl paraben, or a mixture thereof.

In a further aspect of this invention, the present invention is novel for use in treatment of various immunoproliferative, and inflammatory skin conditions such as psoriasis, atopic dermatitis, contact dermatitis and other eczematous dermatitis. Other skin conditions, that may be treated with the current invention include seborrhoeic dermatitis, neurodermatitis, lichen planus, ichthyosis vulgaris, pemphigus, bullate pemphigoid, epidermolysis bullosa, urticaria, angioedemas, erythema, lupus erythematosus. Still other conditions that can be treated with this invention include alopecia greata and hair follicular growth problems. These applications are novel in that the present invention provides a new approach for increasing effectiveness and flexibility for treating these disorders.

The foregoing objects and advantages of the invention are illustrative of those that can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variation which may be apparent to those skilled in the art. Accordingly, the present invention resides in the novel, 2 part formulation, formulation compositions and utilization of mechanical enhancement systems as herein described.

EXAMPLES

Example 1

The following as shown in Table 1 are exemplary of compositions for the App A component, which can be formulated within the scope of this invention. These are for illustrative purpose only and are not intended to define the scope of the invention. Formulations are prepared through combining components with compatible mixing properties at elevated temperatures and then mixing components together while lowering the temperature, followed by adding those components with greater thermolability. All compositions are presented by % weight per volume. The cetylated fatty esters have been described under DETAILED DESCRIPTION OF THE INVENTION. For these examples, the following cetylated fatty esters used in combinations of 3 or more have been found to have utility: Cetyl arginine, Cetyl 11-cyclohexylundecanoate, Cetyl decanoate, Cetyl dihomo-γ-linolenate, Cetyl docosapentanoate, Cetyl eicosapentanoate, Cetyl isolaurate, Cetyl laurate, Cetyl linolenate, Cetyl 13-methyl myristate, Cetyl myristoleate, Cetyl myristate, Cetyl oleate, Cetyl ornithine, Cetyl palmitate, Cetyl palmitoleate, Cetyl stearate and Cetyl stearidonate.

TABLE 1

Exemplary Compositions for the App A Component

| Ingredient | Formulation AA | Formulation AB | Formulation AC | Formulation AD | Formulation AE | Formulation AF |
|---|---|---|---|---|---|---|
| ALPHA LIPOIC ACID | 1.00 | 1.00 | 2.00 | 2.00 | 4.00 | 4.00 |
| ASCORBIC ACID | 1.00 | — | 1.00 | 2.00 | 2.00 | — |
| CARBOPOL 934NF | — | — | 0.80 | 0.70 | — | 0.40 |
| CARBOPOL 940 | 0.80 | 0.70 | — | — | 0.40 | — |
| CETO STEARYL ALCOHOL | 2.00 | 2.00 | 1.00 | — | 1.00 | 2.00 |
| CETYL FATTY ESTERS | 6.00 | 5.60 | 7.00 | 8.00 | 5.60 | 10.00 |
| CREMOPHORE RH40 | 2.00 | 1.00 | — | 2.00 | 1.00 | 1.00 |
| DIMETHICONE COPOLYOL | — | — | — | — | 0.20 | 0.20 |
| DISODIUM EDTA | 0.10 | 0.10 | 0.10 | 0.10 | 0.10 | 0.10 |
| ETHYLENE GLYCOL | 2.00 | — | 8.00 | — | 8.00 | — |
| FRAGRANCE | ≦0.20 | ≦0.20 | ≦0.20 | ≦0.20 | ≦0.20 | ≦0.20 |
| GLYCERIN | 2.00 | 2.00 | 2.00 | 2.00 | 2.00 | 2.00 |
| METHYLCOBALAMIN | 0.02 | 0.07 | 0.07 | 0.07 | 0.02 | 0.02 |
| NIACINAMIDE | 5.00 | 2.00 | 5.00 | 2.00 | 2.00 | 5.00 |
| PEG 100 | 6.00 | — | 2.00 | — | — | 2.00 |
| PEG 100 STEARATE | — | — | 2.00 | — | 6.00 | — |
| PEG 500 | — | — | — | 4.00 | — | 1.00 |
| POLYSORBATE 80 | 2.00 | — | 1.00 | — | — | 1.00 |
| PROPYLENE GLYCOL | 5.00 | 12.00 | — | 10.00 | — | 6.00 |
| BENZYL ALCOHOL | 0.60 | — | 0.20 | — | — | 0.60 |
| METHYL PARABEN | — | 0.20 | 0.10 | 0.20 | 0.20 | — |
| PROPYL PARABEN | — | 0.02 | — | 0.02 | 0.02 | — |
| TRICLOSAN | 0.20 | — | 0.20 | — | — | 0.20 |
| CYCLOMETHICONE | — | — | 2.00 | — | — | 1.00 |
| DIMETHICONE | 1.00 | — | — | 1.00 | — | 1.00 |
| SIMETHICONE | — | — | — | — | 1.00 | — |
| AMMONIA BASE | — | — | to pH 6.5 | — | — | to pH 7.0 |
| DIETHANOLAMINE | to pH 6.0 | — | — | — | — | — |
| TRIETHANOLAMINE | — | to pH 6.5 | — | to pH 6.5 | to pH 7.0 | — |
| TOCOPHEROL ACETATE | 2.20 | 1.20 | 1.20 | 1.20 | 1.20 | 1.20 |
| FILTERED PURIFIED AQUA | QS | QS | QS | QS | QS | QS |
| Hypersensitivity/Irritation Patch Test (Normal Skin) | No Irritation or hypersensitivity noted for any of formulations tested from 30 minutes to 5 days observation after removal of the 48 hr patch | | | | | |

These and other App A compositions were evaluated for cream consistency and stability, response of skin to treatment applications and usage preferences.

Example 2

The following as shown in Table 2 are exemplary of compositions for the App B component, which can be formulated within the scope of this invention. These are also for illustrative purpose only and are not intended to define the scope of the invention. Formulations are prepared through combining components with compatible mixing properties at elevated temperatures and then mixing components together while lowering the temperature, followed by adding those components with greater thermolability. The cetylated fatty esters have been described under DETAILED DESCRIPTION OF THE INVENTION. For these examples, the cetylated fatty esters used in App B combinations are the same as the corresponding cetylated fatty esters used for App A when both components were used together for treatment purposes.

These and other App B compositions were evaluated for cream, gel, lotion, foam or ointment consistency and stability, response of skin to treatment applications and usage preferences.

TABLE 2

Exemplary Compositions for the App B Component

| Ingredient | Formulation BA | Formulation BB | Formulation BC | Formulation BD | Formulation BE | Formulation BF |
|---|---|---|---|---|---|---|
| ALPHA LIPOIC ACID | 1.00 | — | 2.00 | — | 2.00 | — |
| CARBOPOL 934NF | — | 0.70 | 0.40 | — | — | — |
| CARBOPOL 940 | — | — | — | 0.70 | 0.80 | — |
| CARBOPOL AQUA CC | 1.00 | — | — | — | — | 0.80 |
| CETO STEARYL ALCOHOL | — | 2.00 | — | 2.00 | — | — |
| CETYL FATTY ESTERS | 5.00 | 7.00 | 9.00 | 6.00 | 8.00 | 10.00 |
| CREMOPHORE RH40 | 1.00 | 2.00 | — | 1.00 | 1.00 | 1.00 |
| DIMETHICONE COPOLYOL | — | — | 0.30 | — | — | — |
| DISODIUM EDTA | 0.10 | 0.10 | 0.10 | 0.10 | 0.10 | 0.10 |
| ETHYLENE GLYCOL | 5.00 | — | — | — | 7.00 | — |

TABLE 2-continued

Exemplary Compositions for the App B Component

| | Concentration (% w/v) | | | | | |
|---|---|---|---|---|---|---|
| Ingredient | Formulation BA | Formulation BB | Formulation BC | Formulation BD | Formulation BE | Formulation BF |
| FRAGRANCE | ≦0.20 | ≦0.20 | ≦0.20 | ≦0.20 | ≦0.20 | ≦0.20 |
| GLYCERIN | 2.00 | — | — | — | 0.02 | 0.04 |
| CITRIC ACID | 2.00 | — | — | — | — | — |
| GLYCOLIC ACID | — | 8.00 | — | — | — | — |
| LACTIC ACID | 2.00 | — | 2.00 | — | 2.00 | — |
| MALLIC ACID | — | — | 2.00 | — | — | — |
| SALICYLIC ACID | — | — | — | 2.00 | 5.00 | 5.00 |
| PEG 100 | 10.00 | — | 2.00 | — | — | 2.00 |
| PEG 100 STEARATE | — | — | 2.00 | — | 6.00 | — |
| PEG 500 | — | 5.00 | — | — | — | 1.00 |
| PROPYLENE GLYCOL | — | 8.00 | 12.00 | 12.00 | — | 8.00 |
| BENZYL ALCOHOL | 0.60 | — | 0.20 | — | — | 0.60 |
| METHYL PARABEN | — | 0.20 | 0.10 | 0.20 | 0.20 | — |
| PROPYL PARABEN | — | 0.02 | — | 0.02 | 0.02 | — |
| TRICLOSAN | 0.20 | — | 0.20 | — | — | 0.20 |
| CYCLOMETHICONE | — | 2.00 | 2.00 | — | — | 1.00 |
| DIMETHICONE | 1.00 | — | — | 1.00 | — | — |
| SIMETHICONE | — | — | — | — | 1.00 | 1.00 |
| AMMONIA BASE | — | to pH 5.5 | — | — | — | — |
| DIETHANOLAMINE | to pH 5.5 | — | to pH 4.5 | — | — | — |
| TRIETHANOLAMINE | — | — | — | to pH 4.5 | to pH 6.0 | to pH 4.5 |
| TOCOPHEROL ACETATE | 2.20 | 1.20 | 1.20 | 1.20 | 1.20 | 1.20 |
| FILTERED PURIFIED AQUA | QS | QS | QS | QS | QS | QS |
| Physical Characteristics | Stable moderate viscosity | Stable Cream, good consistency | Stable Cream, lower viscosity | Stable Cream, good consistency | Stable higher viscosity Cream | Stable higher viscosity |
| Hypersensitivity/Irritation Patch Test (Normal Skin) | No Irritation or hypersensitivity noted for any of formulations tested from 30 minutes to 5 days observation after removal of the 48 hr patch | | | | | |

Example 3

An open label study was initiated with 36 volunteers (8 males, 28 females). Of those, only participants with mild to moderate psoriatic conditions were chosen (i.e., those with PASI scores of ≦10, severe, were excluded from analysis). Participants had lesions over ≦29% of total body and all demonstrated various degrees of lesion severity from slight to moderate as defined by PASI score (Psoriasis Area and Severity Index). The App A component was applied twice daily on all body areas where lesions manifested, as per guidelines. The App B component was applied only to lesions 2-3 times a week. Patients were observed in 4 visits with baseline established as week 0 and subsequent visits at weeks 1, 3 and 5. Physician observations of patients were quantified using Results: Results for the study are presented in Table 3 as the averages and standard errors for the total PASI score and the individual severity indicators. All patients showed improvements during the study period as indicated by changes in PASI scores. The primary desired outcome (PASI 60) was observed by week 3 and also week 5. The most significant treatment effects were in the reduction of erythema. Full factorial analysis of variance found significant changes from baseline in the total PASI index and in the change in erythema by weeks 3 and 5. However, treatment was also observed to reduce the average severity of psoriasis scaling and thickness by more than 40% by the end of the $5^{th}$ week. The results are presented in FIG. 1 as the mean index of change from baseline for total PASI Score, erythema, thickness and scaling. An efficacy of this two-treatment process is indicated for mild to moderate psoriasis through this example.

TABLE 3

Average Treatment Score Analyses

| Score Parameter | Week of Visit- Average (Standard Error) | | | | ANOVA Wk 0 vs Wk 3 | ANOVA Wk 0 vs Wk 5 |
|---|---|---|---|---|---|---|
| | 0 | 1 | 3 | 5 | | |
| Total PASI | 8.07 (0.18) | 5.97 (1.18) | 4.17 (1.00) | 3.00 (0.44) | 0.018 | <0.001 |
| Erythema | 7.00 (0.58) | 4.67 (0.67) | 3.33 (0.67) | 2.33 (0.33) | 0.014 | 0.002 |
| Thickness | 7.33 (1.45) | 5.00 (1.15) | 4.67 (1.20) | 4.00 (0.58) | 0.230 | 0.100 |
| Scaling | 7.00 (1.15) | 5.33 (0.33) | 4.67 (0.33) | 4.00 (0.58) | 0.124 | 0.081 |

PASI Scoring. The Psoriasis Area & Severity Index is a measure of overall psoriasis severity & coverage. It combines the severity (erythema, induration and desquamation) and percentage of affected area. A primary desired outcome was to find a 40% decrease in Average PASI score by end of treatment period (PASI 60).

What is claimed is:

1. A method for the treatment of psoriasis by use of a topical step-wise polytherapy, to a person in need thereof, comprising steps 1 and 2:
   Step 1) Topically applying daily to a symptomatic portion of the skin a first composition comprising:

a) 4 to 40% of 4 or more cetylated fatty esters selected from the group consisting of cetyl arginine, cetyl 11-cyclohexylundecanoate, cetyl decanoate, cetyl dihomo-γ-linolenate, cetyl docosapentanoate, cetyl eicosapentanoate, cetyl isolaurate, cetyl laurate, cetyl linolenate, cetyl 13-methyl myristate, cetyl myristoleate, cetyl myristate, cetyl oleate, cetyl ornithine, cetyl palmitate, cetyl palmitoleate, cetyl stearate, cetyl stearidonate and those having saturated or unsaturated hydrocarbon chains having 10 or more carbon atoms;
b) 5 to 30% of one or more polar solvents selected from the group consisting of propylene glycol, glycerol, ethylene glycol, 1,2,6-hexane triol, 1,2,4-butane triol, propylene glycol ether of methyl glucose or sorbitol, PEG 40 hydrogenated castor oil, dimethicone copolyol and polyethylene glycol; and
c) a pharmaceutically acceptable vehicle; and
Step 2) Topically applying a second composition, 2-3 times a week to the same portion of skin as the first composition, wherein the second composition comprises:
a) 4 to 40% of 4 or more cetylated fatty esters selected from the group consisting of cetyl arginine, cetyl 11-cyclohexylundecanoate, cetyl decanoate, cetyl dihomo-γ-linolenate, cetyl docosapentanoate, cetyl eicosapentanoate, cetyl isolaurate, cetyl laurate, cetyl linolenate, cetyl 13-methyl myristate, cetyl myristoleate, cetyl myristate, cetyl oleate, cetyl ornithine, cetyl palmitate, cetyl palmitoleate, cetyl stearate, cetyl stearidonate and those having saturated or unsaturated hydrocarbon chains having 10 or more carbon atoms;
b) 1 to 20% of a keratolytic agent; and
c) a pharmaceutically acceptable vehicle.

2. The method according to claim 1, wherein the first composition further comprises one or more cobalamins, at a concentration ranging from 0.05 to 8%, wherein the cobalamins are selected from the group consisting of methylcobalamin, hydroxocobalamin, adenosylcobalamin, cyanocobalamin, isovitamin B12, adenylpropylcobalamin, dihydroxypropylcobalamin, and methyl-10-chlorocobalamin.

3. The method according to claim 2, wherein the first composition further comprises one or more niacinamides and niacinamide derivatives, at a concentration ranging from 1 to 10%, wherein the niacinamides or niacinamide derivatives are selected from the group consisting of 6-aminonicotinamide, 6-carbamoylnicotinamide, 6-chloronicotinamide, 6-dimethylamino-nicotinamide, 6-aminonicotinic acid methyl ester, 6-hydroxy nicotinic acid, thionicotinamide, 2-aminopyrazinamide, 2-carbamoylpyrazinamide, 6-benzoylamino nicotinamide, 6-oxalylamino nicotinamide, 6-malonylamino nicotinamide, 6-succinylamino nicotinamide, 6-glutarylamino nicotinamide ethyo or methyl ester, 6-phosphorylamino nicotinamide, 1-methyl-6-keto-1,6-dihydronicotinamide, 1-methyl-6-keto-1,6-dihydronicotinic acid, methyl 1-methyl-6-keto-1,6-dihydronicotinate and ethyl 1-methyl-6-keto-1,6-dihydronicotinamide.

4. The method according to claim 2, wherein the first composition has a pH ranging from 5.0 to 7.0.

5. The method according to claim 1, wherein the keratolytic agent of the second composition is selected from the group consisting of glycolic acid, salicylic acid, citric acid, isocitric acid, glucuronic acid, galacturonic acid, glucuronolactone, α-hydroxybutyric acid, lactic acid, mallic acid, mandelic acid, muric acid, pyruvic acid and esters thereof, β-phenyllactic acid, β-phenylpyruvic acid, β-hydroxybutyric acid, tartaric acid and tartronic acid.

6. The method according to claim 5, wherein the second composition further comprises one or more polar solvents, at a concentration ranging from 1 to 20%, wherein the polar solvent is selected from the group consisting of propylene glycol, glycerol, ethylene glycol, 1,2,6-hexane triol, 1,2,4-butane triol, propylene glycol ether of methyl glucose or sorbitol, PEG 40 hydrogenated castor oil, dimethicone copolyol and polyethylene glycol.

7. The method according to claim 5, wherein the second composition has a pH ranging from 4.0 to 6.0.

8. A method for the treatment of skin disorders relating to skin dermatitis, eruptions or lesions, by use of a topical stepwise polytherapy, to a person in need thereof, the method comprising steps 1 and 2:
Step 1) Topically applying daily to a symptomatic portion of the skin and surrounding asymptomatic portions of the skin a first composition comprising:
a) 4 to 40% of 4 or more cetylated fatty esters selected from the group consisting of cetyl arginine, cetyl 11-cyclohexylundecanoate, cetyl decanoate, cetyl dihomo-γ-linolenate, cetyl docosapentanoate, cetyl eicosapentanoate, cetyl isolaurate, cetyl laurate, cetyl linolenate, cetyl 13-methyl myristate, cetyl myristoleate, cetyl myristate, cetyl oleate, cetyl ornithine, cetyl palmitate, cetyl palmitoleate, cetyl stearate, cetyl stearidonate and those having saturated or unsaturated hydrocarbon chains having 10 or more carbon atoms;
b) 5 to 30% of one or more polar solvents selected from the group consisting of propylene glycol, glycerol, ethylene glycol, 1,2,6-hexane triol, 1,2,4-butane triol, propylene glycol ether of methyl glucose or sorbitol, PEG 40 hydrogenated castor oil, dimethicone copolyol and polyethylene glycol; and
c) a pharmaceutically acceptable vehicle;
Step 2) Topically applying a second composition, 2-3 times a week, only to the symptomatic portions of skin, wherein the second composition comprises:
a) 4 to 40% of 4 or more cetylated fatty esters selected from the group consisting of cetyl arginine, cetyl 11-cyclohexylundecanoate, cetyl decanoate, cetyl dihomo-γ-linolenate, cetyl docosapentanoate, cetyl eicosapentanoate, cetyl isolaurate, cetyl laurate, cetyl linolenate, cetyl 13-methyl myristate, cetyl myristoleate, cetyl myristate, cetyl oleate, cetyl ornithine, cetyl palmitate, cetyl palmitoleate, cetyl stearate, cetyl stearidonate and those having saturated or unsaturated hydrocarbon chains having 10 or more carbon atoms;
b) 1 to 20% of a keratolytic agent; and
c) a pharmaceutically acceptable vehicle;
wherein the skin disorder is selected from the group consisting of psoriasis, atopic dermatitis, seborrheic dermatitis, nummular eczema, ichthyosis vulgaris, keratosis pilaris, pemphigus and bullate pemphigoid.

* * * * *